(12) United States Patent
Botta et al.

(10) Patent No.: US 8,685,953 B2
(45) Date of Patent: Apr. 1, 2014

(54) LINEAR AND CYCLIC GUANIDINE DERIVATIVES, METHOD OF PREPARATION AND USES THEREOF

(75) Inventors: Maurizio Botta, Siena (IT); Francesco Raffi, Siena (IT); Paolo Visca, Siena (IT)

(73) Assignee: Universita Degli Studi Di Siena, Siena (IT)

(*) Notice: Subject to any disclaimer, the term of this patent is extended or adjusted under 35 U.S.C. 154(b) by 272 days.

(21) Appl. No.: 12/922,232

(22) PCT Filed: Mar. 12, 2009

(86) PCT No.: PCT/IB2009/051032
§ 371 (c)(1),
(2), (4) Date: Oct. 15, 2010

(87) PCT Pub. No.: WO2009/113033
PCT Pub. Date: Sep. 17, 2009

(65) Prior Publication Data
US 2011/0039854 A1   Feb. 17, 2011

Related U.S. Application Data

(60) Provisional application No. 61/036,165, filed on Mar. 13, 2008.

(51) Int. Cl.
*C07D 255/02* (2006.01)
*C07D 259/00* (2006.01)
*A61K 31/395* (2006.01)
*A61P 31/10* (2006.01)

(52) U.S. Cl.
USPC .......................................... 514/183; 540/460

(58) Field of Classification Search
USPC .......................................... 540/460; 514/183
See application file for complete search history.

(56) References Cited

U.S. PATENT DOCUMENTS 3,499,927 A   3/1970   Badcock et al.
3,988,370 A   10/1976  Cutler et al.

OTHER PUBLICATIONS

Castagnole, et al., "Macrocyclization of Di-Boc-guanidino-alkylamines related to Synthesis of Innovative Macrocyclic Amidinoureas", European Journal of Organic Chemistry, 2009, pp. 334-337.

*Primary Examiner* — Bruck Kifle
(74) *Attorney, Agent, or Firm* — Lucas & Mercanti, LLP

(57) ABSTRACT

The present invention relates to linear and cyclic guanidine derivatives, method of preparation and uses thereof, pharmaceutical compositions to be used as antifungal agents, in particular against *Candida* species.

9 Claims, No Drawings

LINEAR AND CYCLIC GUANIDINE DERIVATIVES, METHOD OF PREPARATION AND USES THEREOF

CROSS-REFERENCE TO RELATED APPLICATIONS

This application is a 371 of PCT/IB2009/051032 filed Mar. 12, 2009, which claims the benefit of U.S. Application No. 61/036,165 filed Mar. 13, 2008, the contents of each of which are incorporated herein by reference.

TECHNICAL FIELD

The present invention relates to linear and cyclic guanidine derivatives, method of preparation and uses thereof, pharmaceutical compositions to be used as antifungal agents, in particular against *Candida* species.

BACKGROUND OF THE INVENTION

The opportunistic human pathogen *Candida albicans* and other non-*albicans* species have acquired considerable clinical significance as infectious agents in immunocompromised patients, being important causes of morbidity and mortality. The recommended therapy relies on fluconazole, voriconazole and caspofungin. In fact, also many of the new possible antifungal agents that can be found in the literature possess an azole core.

The pathogenic species of *Candida* derive their relevance not only from the severity of the infections but also from their ability to develop resistance against a variety of antifungal agents. In fact, widespread and prolonged use of azoles has led to the rapid development of multidrug resistance, which poses a major hurdle in antifungal therapy. Many of the currently available drugs have become ineffective against new or re-emerging fungi because of the rapid development of resistance. These problems have give rise to the need to develop new effective antifungal agents. Accordingly, in the last years, new structural classes of antifungal agents were reported, among which guanidine derivatives proved to have very interesting inhibitory activity. As an example, guazatine (a mixture of guanidines and polyamines used in agriculture as fungicide) was classified as a moderately hazardous antifungal agent, while results from in vivo animal studies demonstrated a high potential for guazatine and related compounds as antifungal agents. Authors have recently reported that components of guazatine are able to act toward albicans and non-albicans *Candida* species.

SUMMARY OF THE INVENTION

The present invention concerns novel cyclic guanilated derivatives of different polyamines. On the basis of the results obtained with components of guazatine, new cyclic guanidine derivatives of different polyamines have been synthesized, and their biological evaluation against 8 clinical isolates and 3 reference species of *Candida* (*C. albicans* ATCC 60193, *C. krusei* ATCC 14243, *C. parapsilosis* ATCC 34136) has been carried out. The new compounds object of the invention possess an excellent antifungal activity, and they
1. are very active against different species of *Candida*;
2. have a low toxicity
3. are active also against drug resistant strains of *Candida*.

It is further object of the invention to use any of the compounds as a medicament.

It is further object of the invention to use any of the compounds as an anti-infectious agent, preferably as antifungal agent, more preferably as antifungal agent against *Candida* species, even more preferably wherein the *Candida* species belong to the group of *C. albicans, C. krusei, C. parapsilosis*.

It is further object of the invention to provide a pharmaceutical composition comprising any of the compounds claimed herein or a mixture of any of them, and appropriate excipients and diluents. The expert in the field shall select appropriate excipients and diluents according to the way of administration (topic, oral, parenteral, etc.). In a preferred embodiment the composition further comprises at least one other compound with antifungal activity.

It is further object of the invention to provide a process for the preparation of a compound comprising the following steps:

a) reaction of a suitable amine $R_1$—$NH_2$ with a suitable S-methylisothiourea in a suitable solvent for obtaining compound 2

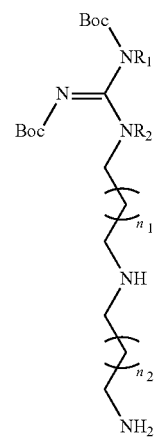

wherein
$n_1$ and $n_2$ are 4 or 6, $n_2$ can be $n_1$ or $n_2$ can be different from $n_1$;
$R_1$=H, propargyl, cyclopropylmethyl, γ-methylallyl, β-methylallyl, γ,γ-dimethylallyl, methyl or ethyl;
$R_2$=H, propargyl, cyclopropylmethyl, γ-methylallyl, β-methylallyl, γ,γ-dimethylallyl, methyl or ethyl;

b) extract and/or purify compound 2 as obtained under a);

c) allow compound 2 to react with an appropriate N,N'-bis (tert-butoxycarbonyl)-N-(alkyl)-S-methylisothiourea under conditions suitable for obtaining the compound 3, or 5-10 shown below:

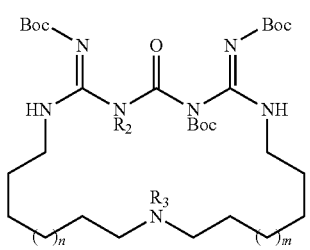

5

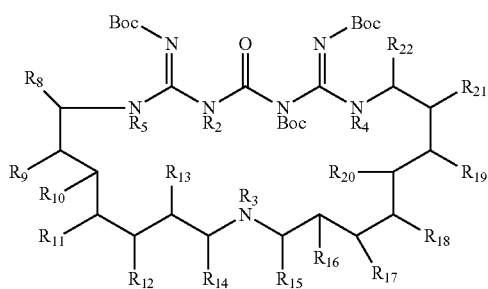

6

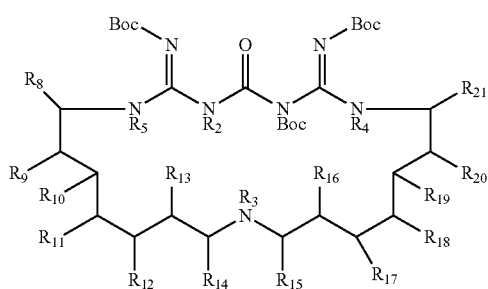

7

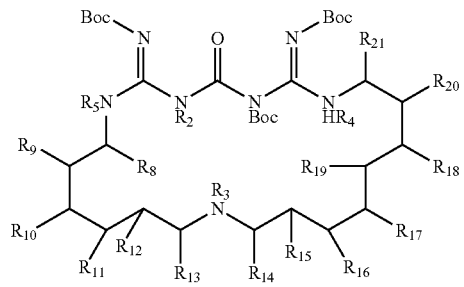

8

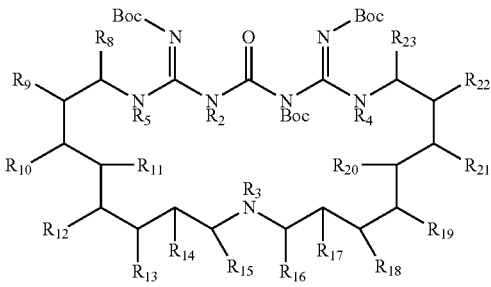

9

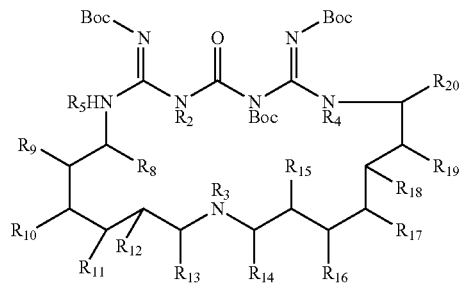

10

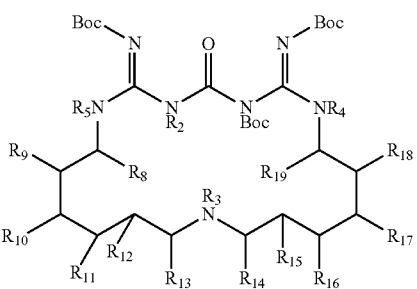

wherein $R_2$=H, propargyl, cyclopropylmethyl, γ-methylallyl, β-methylallyl, γ,γ-dimethylallyl, methyl or ethyl;

$R_3$=H, methyl, ethyl or benzyl;

$R_4$-$R_{23}$=H, methyl or ethyl; $R_4$-$R_{23}$ can be same or different;

d) purify compounds 3, 5-10 as under c);

e) allow compounds 3, 5-10 to react under suitable conditions for obtaining compounds claimed herein;

f) extract and/or purify the compounds as obtained under e).

It is further object of the invention an intermediate of any of formula 3, 5-10:

3

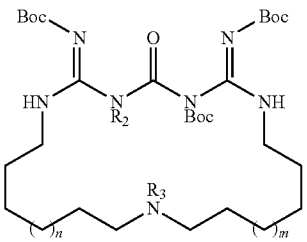

5

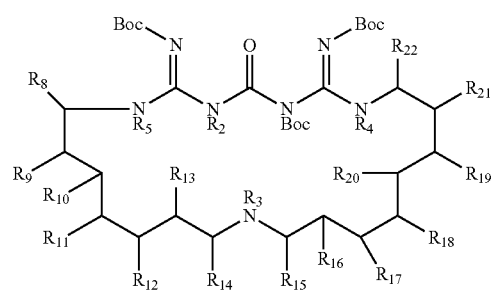

6

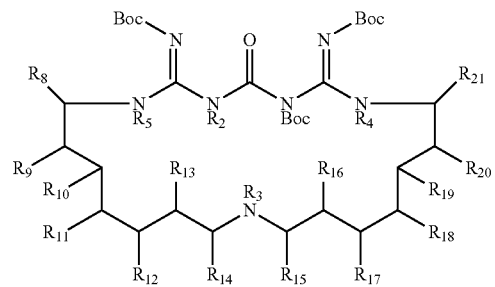

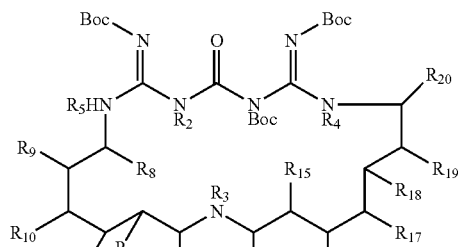
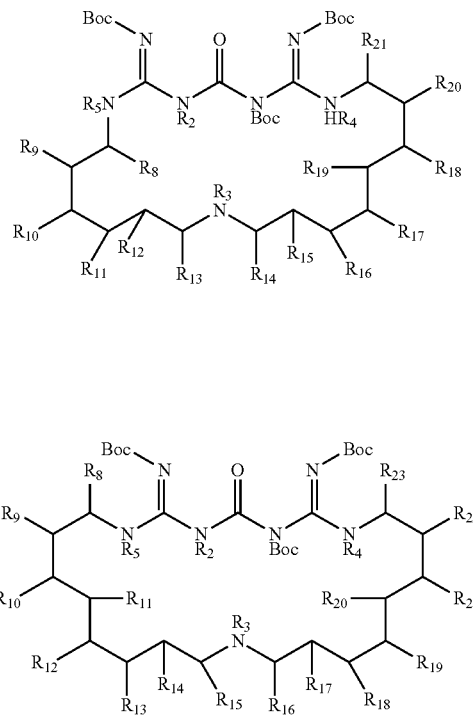
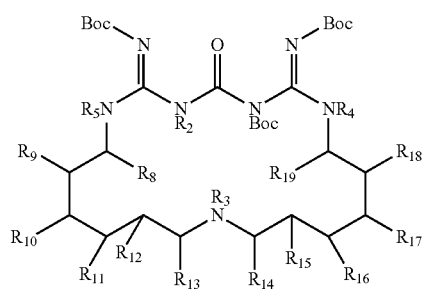
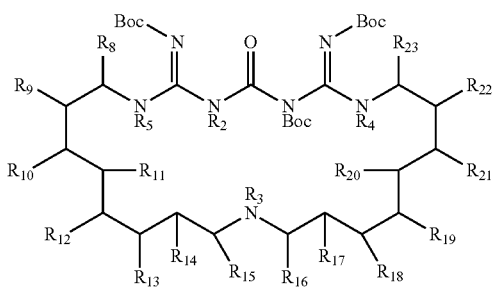
DETAILED DESCRIPTION OF THE INVENTION
Chemistry
The compounds described in this invention can be synthesised as described below:
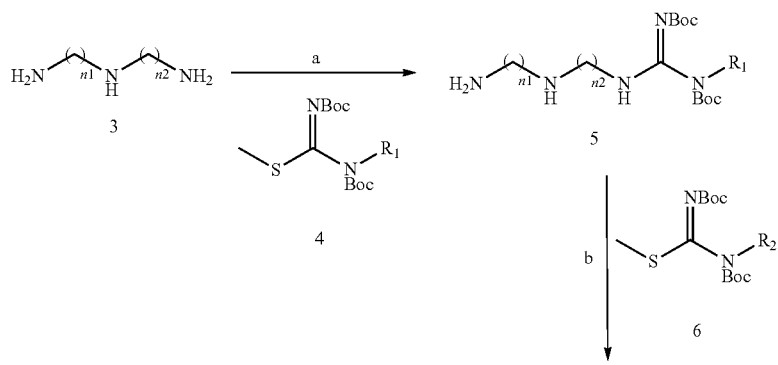
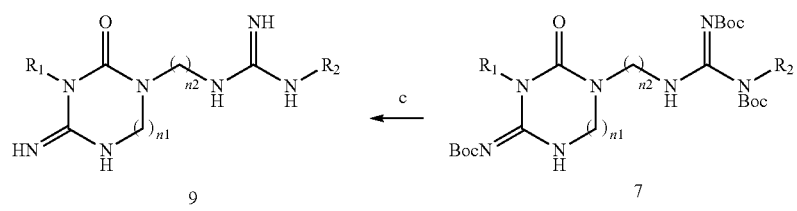
a) THF:MeOH (5:3), 50° C.; b) THF 60° C.; c) 10% TFA, dry $CH_2Cl_2$, 24 h, rt. $R_1$ = H, $R_2$ = H, propargyl, cyclopropylmethyl, benzyl, but-2-enyl, isobutenyl, prenyl $n_1$ and $n_2$ are independently a number from 4 to 8

Examples of the synthetic procedures:

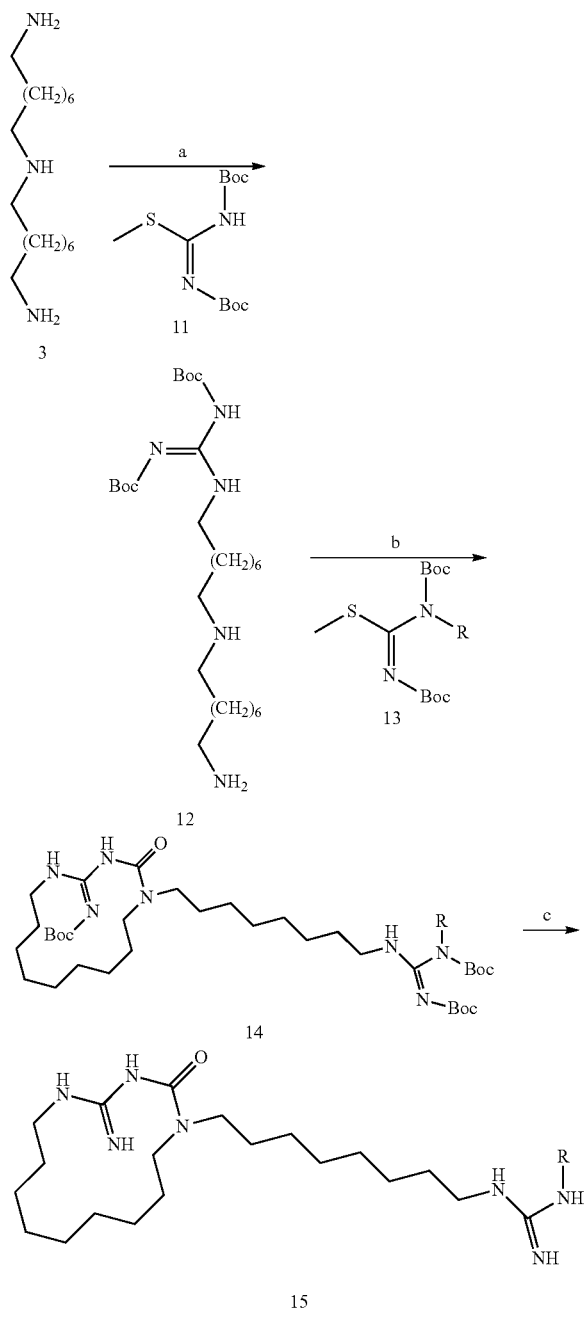

Example 1

Preparation of 1-amino-17-[$N^2,N^3$-bis(tert-butoxycarbonyl)guanidino]-9-azaheptadecane (12)

To a stirred solution of 1,17-diamino-9-azaheptadecane 3 (4.9 g, 15.06 mmol) in THF/CH$_3$OH 5/3 (80 mL) at 50° C., a solution of N,N'-bis(tert-butoxycarbonyl)-S-methylisothiourea (1.456 g, 5.02 mmol) in THF (25 mL) was added dropwise over 1 h. After 16 h, the reaction mixture was concentrated under reduced pressure and the residue was purified by flash chromatography (6% methanol, 4% triethylamine, 90% ethyl acetate), affording 12 as a pale yellow oil, 3.51 g (70%).

Example 2

General Procedure for the Preparation of 14

To a stirred solution of 12 (1.5 mmol) in THF (15 mL) at 60° C., a solution of the appropriate N,N'-bis(tert-butoxycarbonyl)-N-(alkyl)-S-methylisothiourea (1 mmol) in THF (5 mL) was added dropwise. The reaction mixtures were stirred at 60° C. for 16 h, cooled at rt and concentrated under reduced pressure. The crude mixtures were purified by flash chromatography, affording 14a-b as yellow oils.

NMR data for compounds 14a-b

Tert-butyl N-[(2Z)-5-(8-{[(1Z)-{[benzyl][(tert-butoxy)carbonyl]amino}({[(tert-butoxy)carbonyl]imino})methyl]amino}octyl)-4-oxo-1,3,5-triazacyclotridecane-2-ylidene]carbamate (14a)

$^1$H NMR (CDCl$_3$) δ 12.06 (NH, br s), 8.73 (NH, br s), 8.06 (NH, br s), 7.26-7.24 (5H, m), 4.82 (2H, s), 3.47-3.32 (2H, m), 3.25-3.18 (2H, m), 3.00-2.93 (4H, m), 2.01-1.82 (4H, m), 1.48 (9H, s), 1.43 (9H, s), 1.41 (9H, s), 1.29-1.11 (20H, m). MS (ESI): m/z=772.1 [M+H]$^+$.

Tert-butyl N-[(2Z)-5-(8-{[(1Z)-{[propargyl][(tert-butoxy)carbonyl]amino}({[(tert-butoxy)carbonyl]imino})methyl]amino}octyl)-4-oxo-1,3,5-triazacyclotridecan-2-ylidene]carbamate (14b)

$^1$H NMR (CDCl$_3$) δ 8.09 (NH, br s), 4.45 (2H, s), 3.50 (1H, s), 3.45-3.20 (4H, m), 3.25-3.15 (4H, m), 2.01-1.82 (4H, m), 1.48 (9H, s), 1.43 (9H, s), 1.41 (9H, s), 1.32-1.11 (20H, m). MS (ESI): m/z=720.2 [M+H]$^+$.

Example 3

General Procedure for Synthesis of Compounds 15a-15e

Compounds 14a-14e were treated with a 10% solution of freshly distilled TFA in dry DCM (30 mL for 1 mmol) and the reaction mixtures was stirred at rt under argon. After 24 h, the reaction mixtures were concentrated under reduced pressure giving the desired compounds as tri trifluoroacetate salts (brown oils), in quantitative yield. The mixtures were purified by semipreparative HPLC affording the final compounds as tri triformiate salts. NMR data for compounds 15a-15e 1-[benzyl]-3-[8-(4-imino-2-oxo-1,3,5-triazacyclotridec-1-yl)octyl]guanidine tri trifluoroacetate (15a)

$^1$H NMR (CD$_3$)$_2$CO δ 8.25 (NH, br s), 7.75 (NH, br s), 7.44 (NH, br s), 7.35-7.32 (5H, m), 4.55-4.52 (2H, d, J=5 Hz), 3.75-3.44 (4H, m), 3.32-3.29 (4H, m), 1.64-1.57 (8H, m), 1.30 (16 H, br s). MS (ESI): m/z=472.1 [M+H]$^+$.

1-[propargyl]-3-[8-(4-imino-2-oxo-1,3,5-triazacyclotridec-1-yl)octyl]guanidine tri trifluoroacetate (15b)

$^1$H NMR (CD$_3$)$_2$CO δ8.26 (NH, br s), 7.60 (NH, br s), 7.44 (NH, br s), 4.16-4.14 (2H, m), 3.48-3.45 (4H, m), 3.33-3.27 (4H, m), 2.89 (1H, s), 1.68-1.59 (8H, m), 1.35-1.29 (16H, m). MS (ESI): m/z=420.1 [M+H]$^+$.

1-[cyclopropylmethyl]-3-[8-(4-imino-2-oxo-1,3,5-triazacyclotridec-1-yl)octyl]guanidine tri trifluoroacetate (15c)

$^1$H NMR (CD$_3$)$_2$CO δ 8.24 (NH, br s), 7.77 (NH, br s), 7.20 (NH, br s), 5.77-5.45 (2H, m), 3.74-3.71 (2H, m), 3.30-3.25 (4H, m), 3.19-3.12 (4H, m), 1.70-1.46 (12H, m), 1.34-1.26 (16H, m). MS (ESI): m/z=436.2 [M+H]$^+$.

1[β-methylallyl]-3-[8-(4-imino-2-oxo-1,3,5-triazacyclotridec-1-yl)octyl]guanidine tri trifluoroacetate (15d)

$^1$H NMR (CD$_3$)$_2$CO δ 8.30 (NH, br s), 7.58 (NH, br s), 4.93-4.88 (2H, d, J=10 Hz), 3.84-3.82 (2H, m), 3.46-3.40 (4H, m), 3.37-3.20 (4H, m), 1.72 (3H, s), 1.62 (8H, br s), 1.32-1.27 (16H, m). MS (ESI): m/z 436.3 [M+H]$^+$.

1-[γ,γ-dimethylallyl]-3-[8-(4-imino-2-oxo-1,3,5-triazacyclotridec-1-yl)octyl]guanidine tri trifluoroacetate (15e)

$^1$H NMR (CD$_3$)$_2$CO δ 8.22 (NH, br s), 7.90 (NH, br s), 5.28-5.25 (1H, m), 3.74-3.71 (2H, m), 3.40-3.30 (4H, m), 3.20-3.10 (4H, m), 1.65-1.44 (14H, m), 1.30-1.28 (16H, m). MS (ESI): m/z=450.3 [M+H]$^+$.

Biological Tests

Determination of MICs by AFST-EUCAST Standard Methodology

Assay medium. The assay medium was RPMI 1604 without NaHCO$_3$ and with L-glutamine (Sigma Aldrich, Italy), buffered at pH 7.0 with 0.165 M morpholinepropanesulphonic acid (Sigma Aldrich, Italy) and supplemented with 2% (w/v) glucose. The medium, prepared as double-strength solution, was sterilized by filtration and diluted 1:2 (v/v) with the fungal inoculum prepared in sterile distilled water.

Preparation of Inoculate

The yeast isolates were grown on Sabouraud dextrose agar (Oxoid, Madrid, Spain) for 48 h at 37° C. before testing. Suspensions were prepared by combining five distinct colonies of each culture of >1 mm diameter. A spectrophotometric procedure for inoculum preparation was used. The final inoculum suspension, prepared in sterile distilled water, contained between 0.5·10$^5$ and 2.5·10$^5$ cfu/mL.

Antifungal Agents

Stock solutions of test compounds were prepared in 100% dimethyl sulfoxide. Stock solutions were prepared as 100× concentration relative to the highest concentration in the antifungal activity test, and frozen at −70° C. until used.

Susceptibility Testing

Sterile plastic micro titration plates containing flat-bottomed wells were used. The plates contained serial dilution of the antifungal agents with a volume of assay medium of 100 μL/well. Two drug-free medium wells were used as sterility and growth controls. The trays were inoculated with 100 μL/well of the final inoculum, with the exception of sterility control wells. The range of concentrations tested for each drug was 1.25-80 μM. The microtitration plates were incubated at 37° C. for 24 h. The minimal inhibitory concentrations (MICs) were determined at 24 h both visually and spectrophotometrically.

Visual Endpoint Determination

By visual endpoint determination, MICs were determined according to a S-1-R scale, with S (susceptible) indicating an optical clear culture, I (intermediate susceptibility) indicating a slightly hazy culture, and R (resistant) indicating no reduction in turbidity. The MIC$_{50}$ was defined as the lowest concentration of a drug which correspond to a S culture.

Spectrophotometric Endpoint Determination

Microtitration plates were stirred using a microtitration plate shaker before reading to ensure uniform turbidity. MICs were obtained by measuring the absorbance at 450 nm with a microtitration plate reader. The value of the blank was subtracted from reading of the rest of the wells. Two endpoints were defined for each antifungal agent tested, with MIC$_{80}$ indicating the lowest drug concentration resulting in a reduction of growth of 80% or more (determined spectrophotometrically) compared with the growth of the control, and MIC$_{50}$ indicating the lowest drug concentration resulting in a reduction in growth of 50% (determined spectrophotometrically) compared with the growth of the control. The MIC$_{50}$ was also defined as the spectrophotometric endpoint.

Results

The results of the biological tests are shown in Table 1 and Table 2. Compound 15e, bearing the most bulky side chain (a prenyl group), showed interesting activity toward *C. albicans* (20-40 μM), *C. krusei* and *C. tropicalis*, while *C. parapsilosis* and *C. glabrata* were low sensitive to such a compound (40-80 μM). Reducing the size of the unsaturated chain to a butenyl group (15c), activity underwent a significant increase showing very good values toward *C. albicans* (2.5 μM against all strains) and *C. tropicalis* (1.25 μM). *C. krusei* strains were also sensitive, but at a lower concentration (10 μM). Changing the butenyl chain into a methylpropenyl moiety (15d) caused a dramatic loss of activity against all fungal strains. The best activity for this compound was found toward *C. albicans* (MIC=20 μM toward the standard and 15T strains). A further reduction of the side chain size to a propargyl moiety as in 15b restored a good activity toward *C. albicans* (with the exception of *C. albicans* 4T that was resistant to such a compound) and *C. tropicalis* (5 μM). Finally, aromatisation of the side chain to a benzyl group (15a) led to activity data comparable to those found for the butenyl derivative 15c. In summary, both the butenyl and benzyl derivatives showed the best values for antifungal activity, followed by the propargyl compound that retained interesting activity toward a wide number of fungal strains.

TABLE 1

Antifungal activity of guazatine components and linear and cyclic guanidino derivatives.

| | Antifungal activity, expressed as MIC$_{50}$ (μM)$^a$ | | | | | |
|---|---|---|---|---|---|---|
| *Candida* species | 15a | 15b | 15c | 15d | 15e | F |
| *C. albicans* ATCC 60193 | 2.5 | 2.5 | 2.5 | 20 | 40 | 0.8 |
| *C. albicans* 4T | 2.5 | 80 | 2.5 | 40 | 20 | 209 |
| *C. albicans* 53T | 2.5 | 5 | 2.5 | 40 | 20 | 418 |
| *C. albicans* 15T | 5 | 2.5 | 2.5 | 20 | 20 | 209 |
| *C. krusei* ATCC 14243 | 20 | 80 | 10 | 40 | 10 | 209 |
| *C. krusei* 193T | 10 | 40 | 10 | 80 | 20 | 418 |
| *C. parapsilosis* ATCC 34136 | 80 | 40 | >80 | >80 | >80 | 6.5 |
| *C. parapsilosis* 64E | 20 | 40 | 20 | >80 | >80 | 32 |
| *C. parapsilosis* 81E | 20 | 80 | 40 | >80 | 40 | 13 |
| *C. glabrata* 70E | 40 | 80 | 40 | 80 | 80 | 209 |
| *C. tropicalis* 86E | 2.5 | 5 | 1.25 | 40 | 20 | 52 |

$^a$MIC values were determined at 24 h both visually and spectrophotometrically.
F is fluconazole.

TABLE 2

Antifungal activity of guazatine components and linear and cyclic guanidino derivatives.

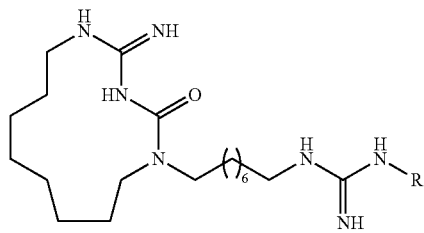

13a R = Benzyl;
13b R = Propargyl;
13d R = But-2-enyl;
13e R = Isobutenyl;
13f R = Prenyl

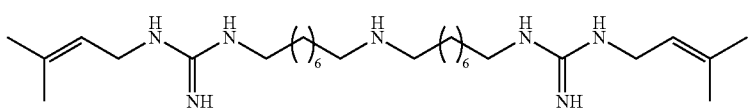

15

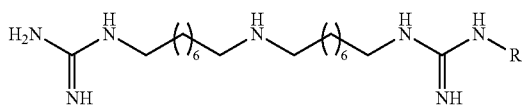

12c R = Methylcyclopropyl
12f R = Prenyl

| | Antifungal activity, expressed as MIC$_{50}$ (μM)$^a$ | | | | | | |
|---|---|---|---|---|---|---|---|
| Candida species | 12c | 12f | 13a | 13b | 13d | 13e | 13f |
| C. albicans ATCC 60193 | 20 | 80 | 2.5 | 2.5 | 2.5 | 20 | 40 |
| C. albicans 4T | 10 | 80 | 2.5 | 80 | 1.25 | 40 | 20 |
| C. albicans 53T | 10 | 80 | 2.5 | 5 | 2.5 | 40 | 20 |
| C. albicans 15T | 20 | 40 | 5 | 2.5 | 1.25 | 20 | 20 |
| C. krusei ATCC 14243 | 5 | 40 | 20 | 80 | 5 | 40 | 10 |
| C. krusei 193T | 10 | 20 | 10 | 40 | 5 | 80 | 20 |
| C. parapsilosis ATCC 34136 | 80 | >80 | 80 | 40 | 5 | >80 | >80 |
| C. parapsilosis 64E | 5 | >80 | 20 | 40 | 5 | >80 | >80 |
| C. parapsilosis 81E | 20 | 40 | 20 | 80 | 5 | >80 | 40 |
| C. glabrata 70E | 20 | 80 | 40 | 80 | 20 | 80 | 80 |
| C. tropicalis 86E | 5 | 20 | 2.5 | 5 | 1.25 | 40 | 20 |

$^a$MIC values were determined at 24 h both visually and spectrophotometrically.

BIBLIOGRAPHY

Chamilos, G.; Kontoyiannis, D. P. *Curr. Opin. Infect. Dis.* 2006, 19, 380.
Aperis, G.; et al., *Expert Opin. Investig. Drugs* 2006, 15, 1319.
Klepser, M. E. *Pharmacotherapy* 2006, 26, 68S.
Pauli, A. *Med. Res. Rev.* 2006, 26, 223.
Buxbaum, A.; et al., *Antimicrob. Chemother.* 2006, 58, 193.
Jana, G. H.; Jain, S.; Arora, S. K.; Sinha, N. *Bioorg. Med. Chem. Lett.* 2005, 15, 3592.
Martin, D. W. et al., *Proc. Natl. Acad. Sci. USA* 1993, 90, 8377.
Dreassi, E.; et al., *J. Pharm. Biomed. Anal.*, in press.
Sheehan, D. J.; Hitchcock, C. A.; Sibley, C. M. *Clin. Microbiol. Rev.* 1999, 12, 40.
Pfaller, M. A. et al., *J. Clinical Microb.* 1999, 37, 870.
Herreros, E. et al., *Antimicrob. Agents Chemother.* 2001, 45, 3132.
Deschenes, R. J.; et al., *Antimicrob. Agents Chemother.* 1999, 43, 1700.

The invention claimed is:

1. A compound having the formula (9):

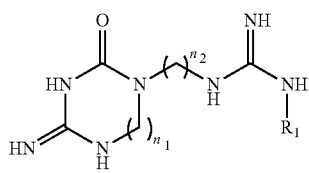

wherein
R$_1$=H, propargyl, cyclopropylmethyl, γ-methylallyl, β-methylallyl or γ,γ-dimethylallyl, benzyl, but-2-enyl, isobutenyl, prenyl, methyl or ethyl;
n$_1$ and n$_2$ are independently a number from 4 to 8, or a pharmaceutically acceptable salt thereof.

2. A pharmaceutical composition comprising an excipient and a compound according to claim 1.

3. The pharmaceutical composition according to claim 2 further comprising at least one other compound with antifungal activity.

4. A process for the preparation of a compound according to claim 1 comprising the following steps in the reaction scheme set forth below:

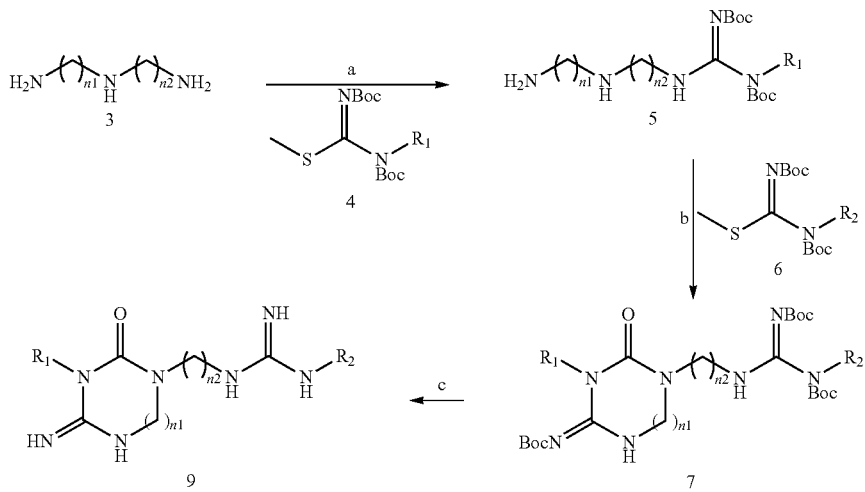

wherein
a) in a mixture of tetrahydrofuran (THF) and methanol (MeOH) in ratio of 5:3 at 50° C.,
b) in THF at 60° C., and
c) in 10% solution of trifluoroacetic acid (TFA) in dry $CH_2Cl_7$ for 24 hours at room temperature, and wherein $R_1$=H
$R_2$=H, propargyl, cyclopropylmethyl, γ-methylallyl, β-methylallyl, γ,γ-dimethylallyl, benzyl, but-2-enyl, isobutenyl, prenyl, methyl or ethyl, and
$n_1$ and $n_2$ are independently a number from 4 to 8.

5. A method for treating a fungal infection in a mammal comprising administering a compound according to claim 1 to the mammal in need thereof, wherein the fungal infection is of a *Candida* species.

6. The method of claim 5, wherein the *Candida* species is selected from the group consisting of *C. albicans, C. krusei* and *C. parapsilosis*.

7. The compound of claim 1, wherein $n_1$ and $n_2$ are independently a number from 6 to 8.

8. The method of claim 4, wherein $n_1$ and $n_2$ are independently a number from 6 to 8.

9. The method of claim 5, wherein $n_1$ and $n_2$ are independently a number from 6 to 8.

\* \* \* \* \*

UNITED STATES PATENT AND TRADEMARK OFFICE
CERTIFICATE OF CORRECTION

PATENT NO. : 8,685,953 B2
APPLICATION NO. : 12/922232
DATED : April 1, 2014
INVENTOR(S) : Maurizio Botta et al.

Page 1 of 1

It is certified that error appears in the above-identified patent and that said Letters Patent is hereby corrected as shown below:

In the Claims

Column 13, line 28 in claim 4,
"$CH_2Cl_7$" should read -- "$CH_2Cl_2$" --.

Signed and Sealed this
Sixth Day of January, 2015

Michelle K. Lee
*Deputy Director of the United States Patent and Trademark Office*

UNITED STATES PATENT AND TRADEMARK OFFICE
CERTIFICATE OF CORRECTION

PATENT NO. : 8,685,953 B2  Page 1 of 1
APPLICATION NO. : 12/922232
DATED : April 1, 2014
INVENTOR(S) : Botta et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 484 days.

Signed and Sealed this

Twenty-ninth Day of September, 2015

Michelle K. Lee
*Director of the United States Patent and Trademark Office*